US 6,564,464 B1

(12) United States Patent
Keating et al.

(10) Patent No.: US 6,564,464 B1
(45) Date of Patent: May 20, 2003

(54) DEVICE AND METHOD FOR THE NON-INVASIVE, EXTERNAL MEASUREMENT OF THE FRANKFORT MANDIBULAR PLANE ANGLE (FMA)

(75) Inventors: Gregory Vail Keating, Silver Spring, MD (US); William Edward Dando, Montgomery Villiage, MD (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 10/090,615

(22) Filed: Mar. 6, 2002

(51) Int. Cl.[7] .............................................. A61B 5/103
(52) U.S. Cl. .......................................... 33/512; 33/464
(58) Field of Search ........................ 33/419, 420, 421, 33/427, 428, 464, 474, 476, 482, 511, 512, 513; 600/587

(56) References Cited

U.S. PATENT DOCUMENTS

| | | | | |
|---|---|---|---|---|
| 637,373 A | * | 11/1899 | Crawford et al. | 33/427 |
| 762,146 A | * | 6/1904 | Cosbie | 33/511 |
| 1,976,045 A | * | 10/1934 | Sorenson | 33/513 |
| 2,107,534 A | * | 2/1938 | Houser | 33/513 |
| 2,154,148 A | * | 4/1939 | Butts | 33/513 |
| 3,377,712 A | * | 4/1968 | Farkas et al. | 33/512 |
| 4,279,260 A | * | 7/1981 | Stump | 600/587 |
| 4,400,826 A | | 8/1983 | Preti et al. | |
| 4,843,720 A | * | 7/1989 | Kim | 33/512 |
| 5,738,515 A | | 4/1998 | Leever | |
| 5,951,498 A | * | 9/1999 | Arnett | 600/587 |
| 6,102,698 A | | 8/2000 | Staples | |

OTHER PUBLICATIONS

DiPietro, *Research and Education,* vol. 38, No. 4, pp 452–458, Oct. 1977.
*Contemporary Orhodonitics,* 3rd Edition, Proffit and Fields, Year Book Medical Publ., 2000, pp160–178.
DiPietro et al., *Prosthet. Dent.,* Dec. 1976.
Dando et al., *J. Dent Res,* 80 (AADR Abstracts) Jan. 2001, Abstract 980.

* cited by examiner

*Primary Examiner*—G. Bradley Bennett
(74) *Attorney, Agent, or Firm*—Barry A. Edelberg; A. David Spevack; Thomas E. McDonnell (57) ABSTRACT

A gauge and a method for using the gauge, measures the Frankfurt Mandibular Angle (FMA) non-invasively, without the use of x-rays. The gauge has an upper bar that, in use, parallels the patient's porion-orbitale line. A downward bar depends from the upper bar and has an adjustably attached lower bar. The lower bar is adjusted to parallel the patient's gonion-menton line. Once the gauge is properly adjusted to the patient and locked into place, the user reads a measuring device on the gauge, which indicates the relative positions of the components of the adjusted gauge. These reading are then correlated, directly or indirectly, to the patient's FMA.

36 Claims, 8 Drawing Sheets

DEVICE AND METHOD FOR THE NON-INVASIVE, EXTERNAL MEASUREMENT OF THE FRANKFORT MANDIBULAR PLANE ANGLE (FMA)

BACKGROUND OF THE INVENTION

1. Field of the Invention

The present invention relates generally to measurement of the Frankfort Mandibular Plane Angle (FMA) and more specifically to the non-invasive, external measurement of FMA, without x-ray.

2. Description of the Background Art

The Frankfurt Mandibular Plane Angle is defined as the angle formed by the intersection of two extended lines: one drawn through the gonion and the second through the porion and orbitale. Traditionally, the FMA is determined by utilizing a lateral cephalometric radiograph, which is developed in an x-ray film processor, dried, labeled and then covered by an acetate sheet. The landmarks are marked, lines traced, and the FMA measured with a protractor. Most recently, charged coupled devices are irradiated in a similar fashion to the lateral cephalogram and the resultant image digitized. The FMA is then determined with the aid of a computer software program after the landmarks are identified. The major limitations and disadvantages of both of these techniques are that invasive x-rays irradiate most of the patient's head, and very costly, cumbersome equipment is required. Also, a skilled dentist, radiologist, or highly trained technician, who has had long experience in tracing these radiographs, must spend time discerning indistinct landmarks, tracing on the acetate coversheet, and "estimating" the FMA with a protractor. Specially shielded x-ray rooms are required when exposing dental x-rays, costly developing machines, and dangerous and harmful chemicals are required. Retakes of the x-ray must be done if the patient moves during exposure or if the head position or degree of mouth opening is not ideal.

SUMMARY OF THE INVENTION

It is an object of the present invention to measure a patient's FMA without invasive procedures and without x-ray.

It is another object of the present invention to measure a patient's FMA without x-rays.

It a further object of the present invention to measure a patient's FMA without expensive special equipment.

These and other objects are achieved by a device that includes a frame having an upper bar and a downward bar extending from the upper bar at a known angle. The upper bar, when fitted to the patient, extends parallel to the patient's porion-orbitale line. The rear bar is fixed to the upper bar extends from the patient's porion to the patient's gonion. A lower bar is movably attached to the rear bar and, when fitted to the patient, extends parallel to and at the same height as the patient's gonion-menton line. Because the relationship between the fixed points of the bars and the fixed points of reference on the patient (porion, orbitale, gonion, and menton) and the dimensions and angular relationships between the various parts of the FMA gauge's frame are known, the FMA can be determined by reading a measuring device on the gauge. In some embodiments, this angular determination can be made directly from the measuring device. In other embodiments, the measuring device indicates the position of the lower bar, once adjusted to the patient, with respect to the downward bar. This relative position may then be correlated with the patient's FMA.

DESCRIPTION OF THE PREFERRED EMBODIMENTS

Figure 1:
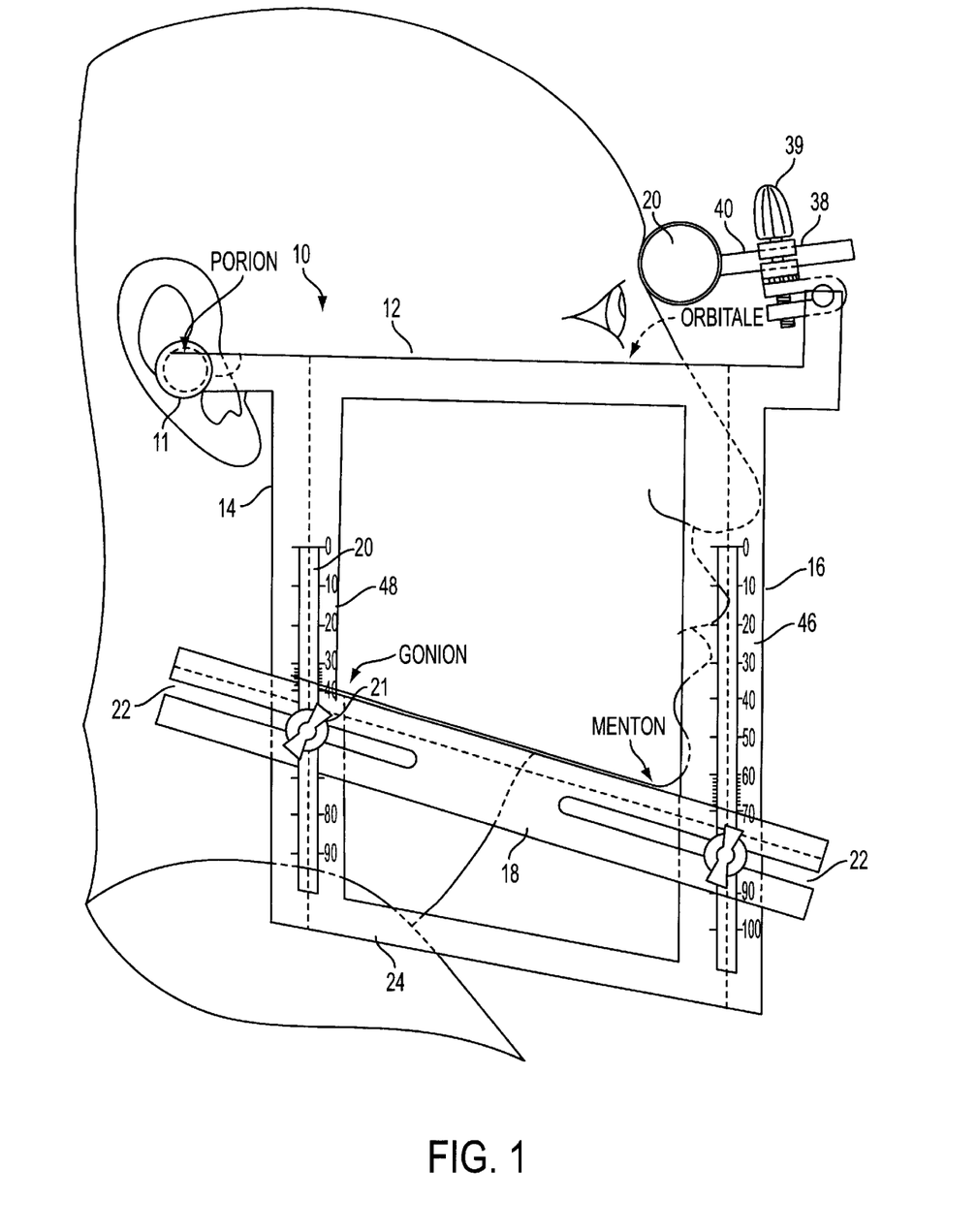
FIG. 1 is a side view of an embodiment of the device according to the present invention.
Figure 2:
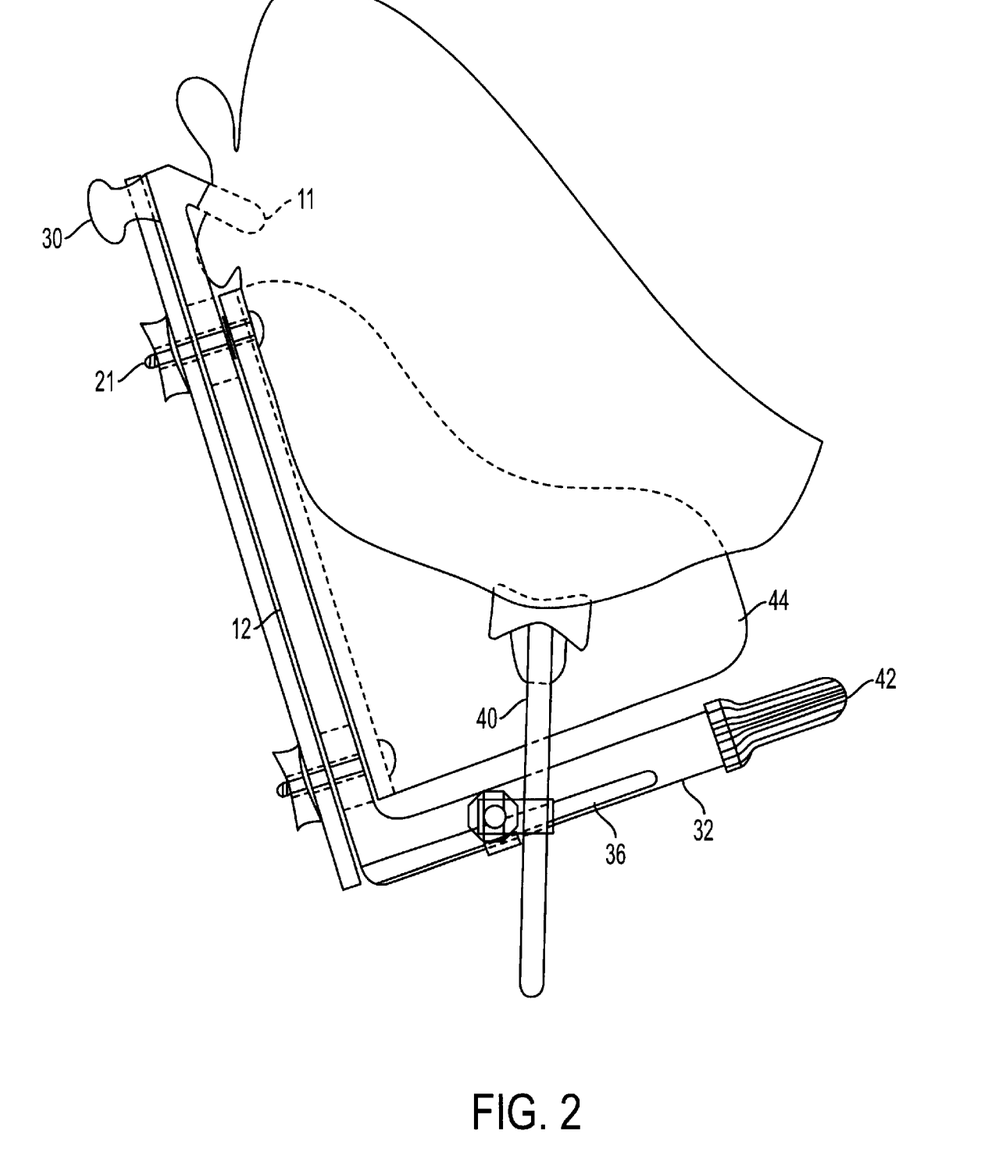
FIG. 2 is a top view of the device shown in FIG. 1

As shown in FIG. 1, FMA gauge 10 includes a frame (typically trapezoidal) having upper bar 12, rear bar 14, front bar 16, and lower bar 18. Upper bar 12 extends at least from the porion to the orbitale of the patient. Upper bar 12 extends parallel to and typically at the same height as the porion-orbitale line. While upper bar 12 could be at height below or above the porion-orbitale line, having it at the same height better enables visual alignment of the gauge parallel to the porion-orbitale line. Additionally, this arrangement allows gauge 10 to be anchored at the porion by earpiece 11 (FIG. 2).

Rear bar 14 is fixed to and extends downwardly from upper bar 12. Generally, rear bar 14 extend to at least the patient's gonion. Rear bar 14 may include a clear or cutout portion 20 which permits the user to visually align the rear bar. 14 with the patient's gonion. In the embodiment of FIG. 1, cutout 20 also serves as a slot allowing lower bar 18 to be upwardly or downwardly adjusted with respect to rear bar 14. While FIG. 1 shows the use of cutout 20 and wingnut 21 to attach lower bar 18 to rear bar 14, any method of attachment that allows lower bar 18 to be adjusted vertically and angularly with respect to rear bar 14 (so that the lower bar can be adjusted to extend parallel to and at the same height as an imaginary line between the patient's gonion and menton), and then locked into position, may be used. For example, lower bar 18 may be attached to rear bar 14 by quick-releasing spring clips fixed to lower bar 18.

As with the attachment of lower bar 18 to rear bar 14, the attachment of rear bar 18 to front bar 16 should allow lower bar 18 to be adjusted vertically and angularly with respect to rear bar 14 (so that the lower bar can be adjusted to extend parallel to and at the same height as an imaginary line between the patient's gonion and menton) and then locked into position. Thus, any attachment method suitable for attachment of lower bar 18 to rear bar 14 should be suitable for the attachment of lower bar 18 to front bar 16. In the embodiment of FIG. 1, lower bar 18 and front bar 16 are attached using the same wingnut and cutout arrangement as used for rear bar 14 and lower bar 18. Lower bar 18 also includes slots to simplify its alignment with the gonion-menton line. Optional support bar 24 is fixed to rear bar 14 and front bar 16, and supports the frame of the gauge.

Figure 4:
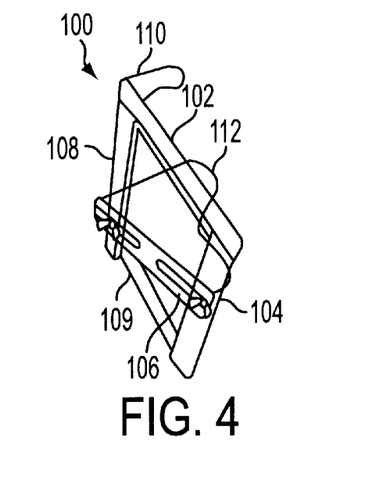
FIG. 4 is an oblique view of a cost-reduced embodiment of a device according to the present invention similar to that shown in FIG. 1.

Although FIG. 4 shows that, in use front bar 16 of gauge 10 attaching to upper bar 12 forward of the menton, The position of front bar 16 with respect to the patient and rear bar 14 are, except for facilitating placement and handling of gauge 10, not critical to the function of the device. Similarly, while FIG. 1 shows rear bar 14 and front bar 16 extending perpendicularly from upper bar 12, the angle between upper bar 12 and the front and rear bars (14, 16) is not critical to the function of the invention. Instead, this invention only requires that the angular relationships and the distances between the parts of the frame are known sufficiently to allow determination of the angle between rear bar 14 and lower bar 21. The device according to the present invention also benefits from a structure that allows the device to be stabilized with a known angular relationship to the orbitale-menton line and with the lower bar parallel to the gonion-menton line.

Figure 3:
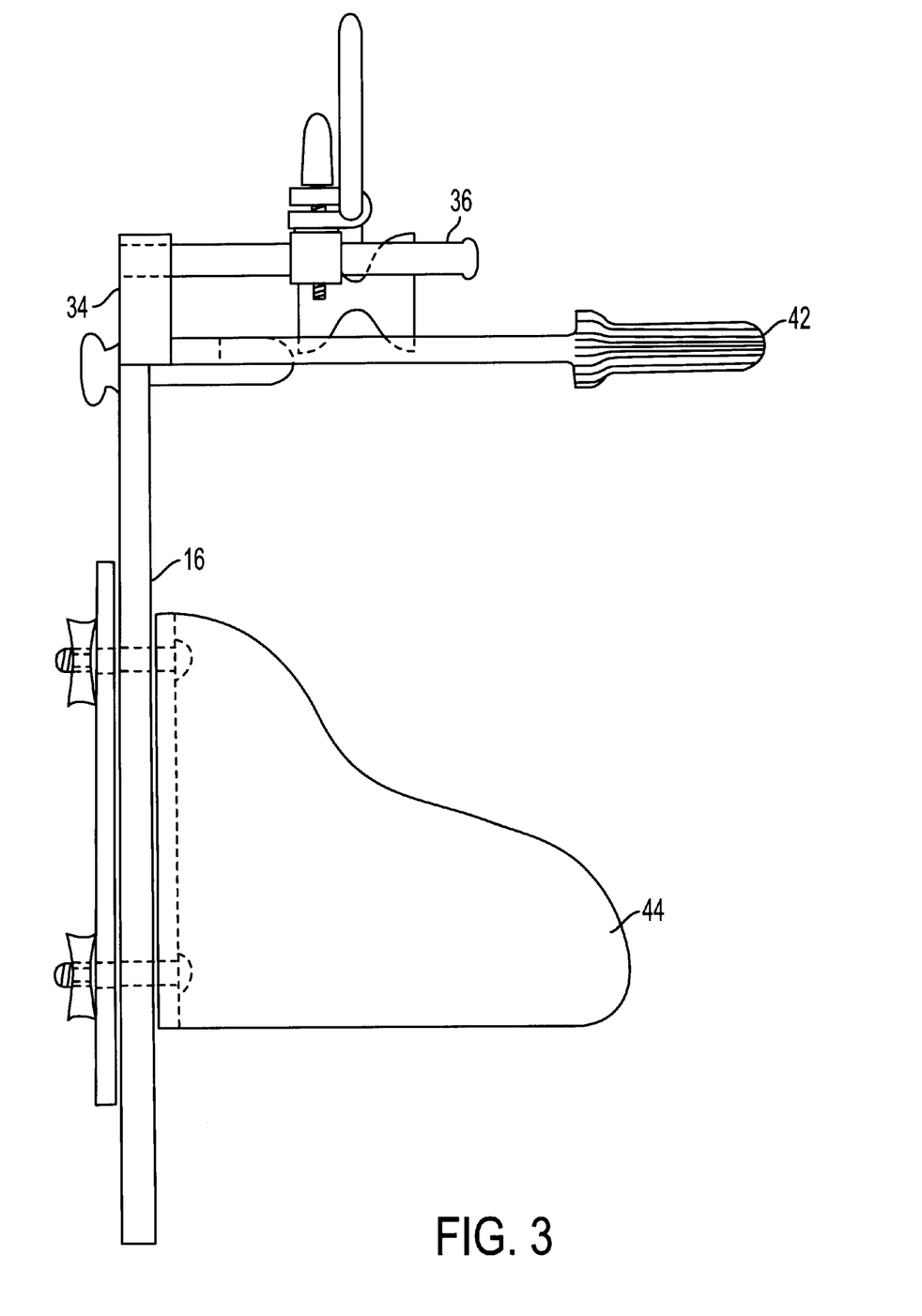
FIG. 3 is a front view of the device shown in FIG. 1 and FIG. 2.

In the device of FIG. 1, stabilization of the device and proper orientation of the device with respect to the patient are aided by the earpiece 11, handle 30 (FIG. 2), face bar 32, nose piece platform 34 (FIG. 3), nosepiece slide 36, universal joint 38, nosepiece 40, handle 42 (FIG. 2), and mandibular plate 44. Typically, mandibular plate 44 is attached to lower bar 18 using the with the same fastening mechanism (such as wingnut 21 and bolt) using to attached lower bar 18 to front and rear bars 16, 14. Therefore, the height and angle of mandibular plate 44 is adjusted simultaneously with that of lower bar 18 Handles 30 and 42 permit the user to more easily position device 10 with respect to the patient. Nose-piece platform 34 attaches nosepiece slide 36 to upper bar 12 so that nosepiece slide 36 extends toward the opposite side of the patient's head, essentially perpendicular to the device's frame, forward of the patient's nose. Nosepiece 40 is attached, at its stem, to nosepiece platform 34 by universal joint 38, which includes a fastener (such as thumbscrew, wingnut, or the like) that can be easily tightened or loosened for facile positioning and locking of nosepiece 40. Nosepiece 40 typically has a dumbbell-shaped end which, when properly adjusted, fits into the bridge of the patient's nose and stabilizes the gauge with respect to the patient. Handle 30, is connected to earpiece 11 and upper bar 12 and facilitates the placement of earpiece 11 in the patient's ear. Handle 30, attached to a portion of upper bar 12 that is essentially perpendicular to the frame, extends towards the opposite side of the patient's head and assists in adjusting the position of nosepiece 40. Mandibular plate 44, is typically attached to front bar 16 and supports the patient's mandible. Once properly fitted, earpiece 11, nosepiece 40, and mandibular plate 44 stabilize device 10 with respect to the patient, thus allowing accurate measurement of the FMA.

In the FIG. 1 embodiment, front bar 16 and rear bar 14 have measuring devices 26 and 48, respectively, for indicating distance along the length of the bar. The measuring devices shown includes scale markings on the bars. Once device 10 is properly adjusted and aligned with respect to the patient, the scale marking at the location where the lower bar 18 intersects front bar 16 and the scale marking at the location where the lower bar 18 intersects rear bar 14 are read and noted. The difference between the markings is then determined. This difference is then entered into an FMA gauge conversion table, such as shown in Table 1, to give the FMA. Whether the scales are read at the forward or rear edges of their respective bars is of course irrelevant, pro-vided that the conversion table is calibrated to the reading method used. If desired, the conversion table may be divided into three sections, one for low FMA, one for average FMA, and another for high FMA.

TABLE 1

FMA GAUGE CONVERSION TABLE

| Low FMA | | Average FMA | | High FMA | |
|---|---|---|---|---|---|
| Difference | FMA in degrees | Difference | FMA in degrees | Difference | FMA in degrees |
| 10 | 5 | 39 | 20 | 65 | 31 |
| 11 | 6 | 40 | 20 | 66 | 31 |
| 12 | 6 | 41 | 20 | 67 | 31 |
| 13 | 7 | 42 | 21 | 68 | 32 |
| 14 | 7 | 43 | 21 | 69 | 32 |
| 15 | 8 | 44 | 22 | 70 | 32 |
| 16 | 8 | 45 | 22 | 71 | 33 |
| 17 | 9 | 46 | 23 | 72 | 33 |
| 18 | 9 | 47 | 23 | 73 | 34 |
| 19 | 10 | 48 | 24 | 74 | 34 |
| 20 | 10 | 49 | 24 | 75 | 34 |
| 21 | 11 | 50 | 24 | 76 | 35 |
| 22 | 11 | 51 | 25 | 77 | 35 |
| 23 | 12 | 52 | 25 | 78 | 35 |
| 24 | 12 | 53 | 26 | 79 | 36 |
| 25 | 13 | 54 | 26 | 80 | 36 |
| 26 | 13 | 55 | 27 | 81 | 36 |
| 27 | 14 | 56 | 27 | 82 | 37 |
| 28 | 14 | 57 | 27 | 83 | 37 |
| 29 | 15 | 58 | 28 | 84 | 37 |
| 30 | 15 | 59 | 28 | 85 | 38 |
| 31 | 16 | 60 | 29 | 86 | 38 |
| 32 | 16 | 61 | 29 | 87 | 38 |
| 33 | 17 | 62 | 29 | 88 | 39 |
| 34 | 17 | 63 | 30 | 89 | 39 |
| 35 | 18 | 64 | 30 | 90 | 39 |
| 36 | 18 | | | 91 | 40 |

Table 1 calculates the FMA using an assumed fixed porion-orbitale distance of 10. Of course the actual porion-orbital distance is irrelevant. Geometrically, the FMA can be determined from the measurements taken at front bar 16 and rear bar 14 provided that the frame is essentially planar, the distance between front bar 16 and rear bar 18 is known, the angle between front bar 16 and upper bar 18 is known, the angle between rear bar 14 and upper bar 18 is known, and the frame is in a known, specified position with respect to the porion-orbital line and the gonion. The trigonometric formula applied for Table 1 uses a predefined "orbital-porion" distance of 110 mm, in the following formula:

$$FMA = \arctan\left(\frac{OM - PG}{OP}\right), \text{ in degrees.}$$

From FIG. 1, its clear that the the FMA can be determined simply by knowing the angle formed by the bar paralleling the GM line and a line paralleling the OP line. Earpiece 11 and nosepiece 40 simply assist in assuring that the device is properly adjusted and stabilized so that the FMA may be measured. The device may be used with the anchoring provided by earpiece 11 and nosepiece 40, although correct alignment and stability may be more difficult to achieve. Additionally, even upper bar 12, or portions thereof (particularly the portions between the front and rear bars 16 and 14) may be removed, albeit at a potential reduction in stability and ease of alignment. As will be shown in embodiments discussed below, front bar 16 may also be removed if, rather than distance measurement along the front and rear bars 16, 14 are made, the angle between lower bar 18 and rear bar 14 is directly measured. Lower bar 24 functions only to aid handling during alignment and increase stability, and is optional.

Typically, device 10 of FIG. 1 is operated as follows:
1. The patient is seated upright, and the operator stands or sits to the right of the patient. After removing eyewear, hearing aides, and any interfering jewelry and pulling back the patient's hair, if necessary, the patient and operator orient themselves so that they are at approximately eye level.
2. The FMA Gauge is prepared by loosening the universal joint 38 just enough to pull the nosepiece 40 toward the front of the gauge; wing nuts 22 are loosened, allowing lower bar 18 to drop downward and forward; and a finger cot is placed over the earpiece 11.
3. The patient or an assistant grips handles 42 and 30 and helps the operator to comfortably guide earpiece 11 into the right ear. The patient or assistant continues to stabilize the FMA Gauge while the operator adjusts the nosepiece 40.
4. The earpiece automatically lines up the top of upper bar 12 with the top of the ear hole, corresponding to the portion. The operator palpates the patient's infraorbital notch and, while lining up the anterior aspect of upper bar 12 with the notch, fits the rubbery, dumbbell-shaped end of nosepiece 40 to the bridge of the nose and tightens the universal joint 40 by twisting the nosepiece adjusting knob 39. The infraorbital notch corresponds to the orbitale.
5. Alignment of upper bar 12 is rechecked for location, fit, and comfort before proceeding to adjust lower bar 18.
6. The patient is asked to swallow and relax the lower jaw, which is then placed into the desired evaluation position. The patient is requested to hold this position while lower bar 18 with attached mandibular plate 44 is raised to firmly contact the lower border of the mandible.
7. Wing nuts 22 are tightened to stabilize the lower bar 18 and mandibular plate 44.
8. A pair of numerical values from the rulers on each of the bars 14, 16 is noted and recorded. In this particular example (using Table 1), the numerical values are derived from where the top of lower bar 18 crosses bars 14, 16. An example of this is shown in FIG. 1. The number from rear bar 14 is subtracted from the number from front bar 16, and the numerical value of the difference is looked up on the FMA Gauge Conversion Table (Table 1). The corresponding Frankfurt Mandibular Angle (FMA) and the descriptive term ("High," "Low" or "Average") are then noted.
9. Repeat measurements are done simply by loosening the wing nuts and dropping down the lower bar 18/mandibular plate 44 assembly. The patient is then allowed to relax for a moment, resume the desired jaw position, device 10 is readjusted, and another measurement is made.
10. Once satisfied with the repeatability of the measurements, the FMA Gauge may now be removed from the patient by reversing the procedure.
11. The finger cot is removed from the earpiece 11 and discarded. The FMA Gauge may now be washed and disinfected.

FIG. 4 shows a cost-reduced version of the FMA gauge of FIG. 1. Frame elements upper bar 102, rear bar 104, lower bar 106, and front bar 108 are analogous their counterparts in the FIG. 1 embodiment, and will not be further described. Also, support bar 109 and mandibular place 112 are analogous to their counterparts and need to be further described.

Figures 5, 6:
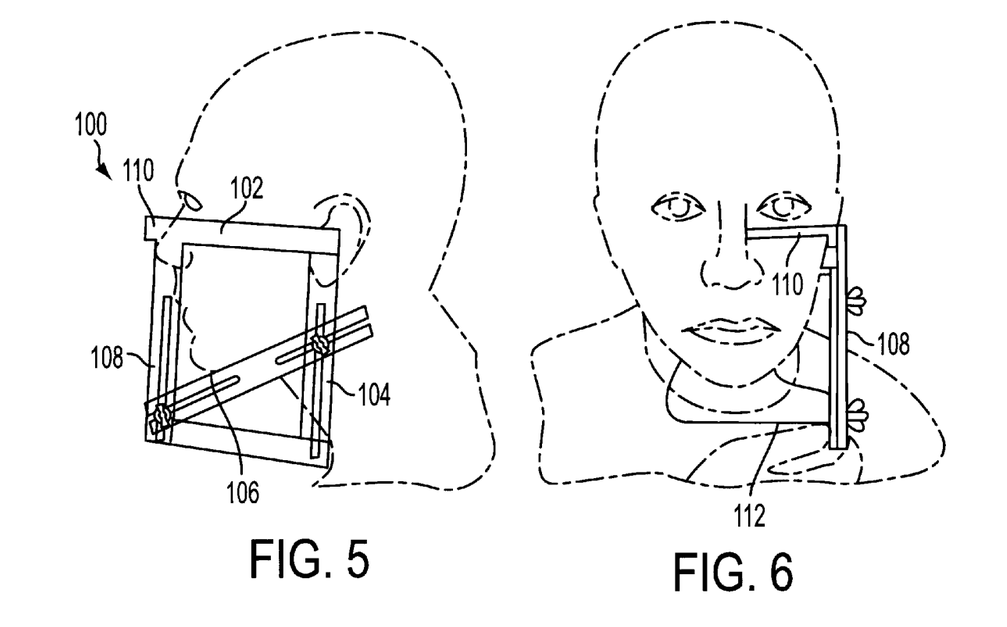
FIG. 5 is a side view of the device shown in FIG. 4, after adjustment to fit the patient.
FIG. 6 is a front view of the device shown in FIG. 4, after adjustment to fit the patient.

The reduced cost embodiment of FIG. 4 lacks the stabilizing earpiece, and, rather than the nosepiece and associated components of the FIG. 1 embodiment, uses infraorbital indicator 110 to provide a reference point for alignment with the patients orbitale and support for stabilizing the device 100 during use. FIG. 5 and FIG. 6 show the device of FIG. 4 properly positioned on at patient. In this embodiment, the intersection of upper bar 102 and rear bar 104 provide a point of reference to align with the porion. If desired, however, a marking along the device, rather than an intersection of frame elements, may serve as the reference point for alignment with the porion. The operation and adjustment of the device shown in FIG. 4 is analogous to that shown in FIG. 1.

Figure 7:
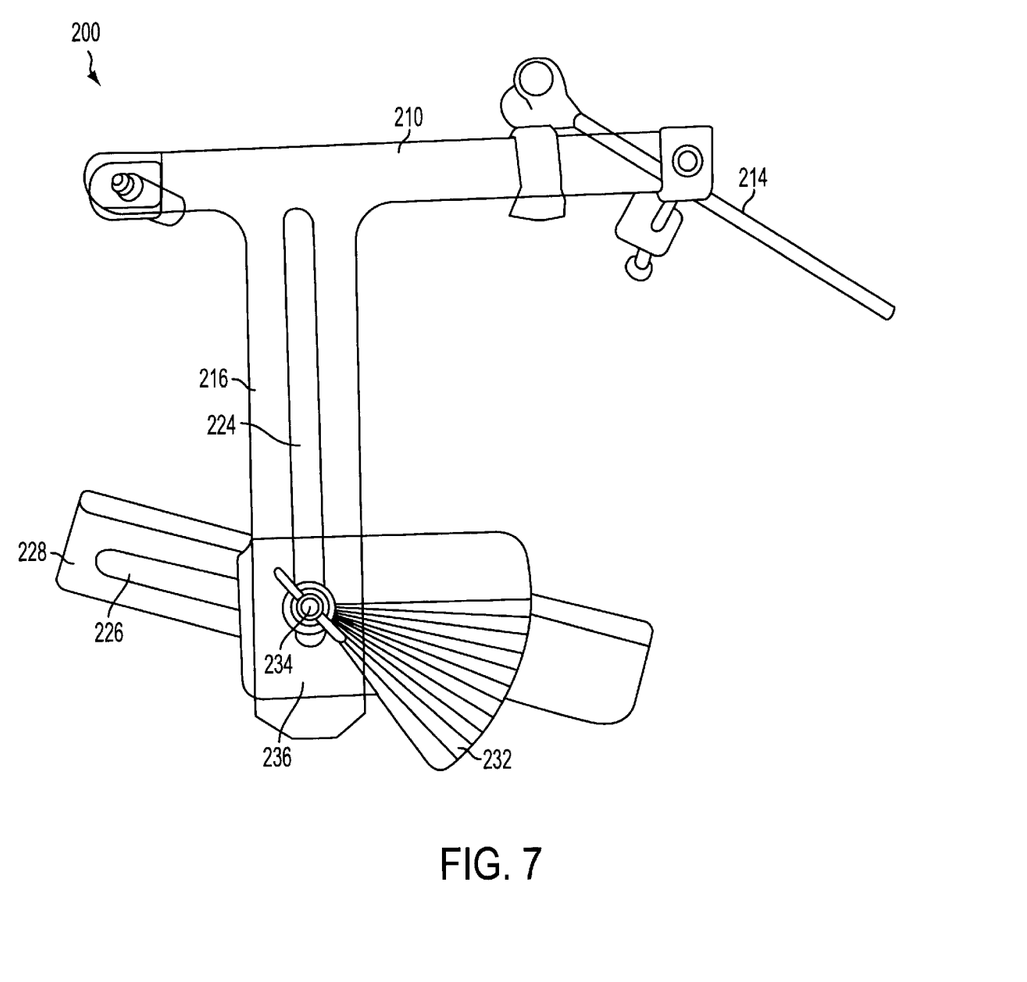
FIG. 7 shows another embodiment of the present invention.
Figure 8:
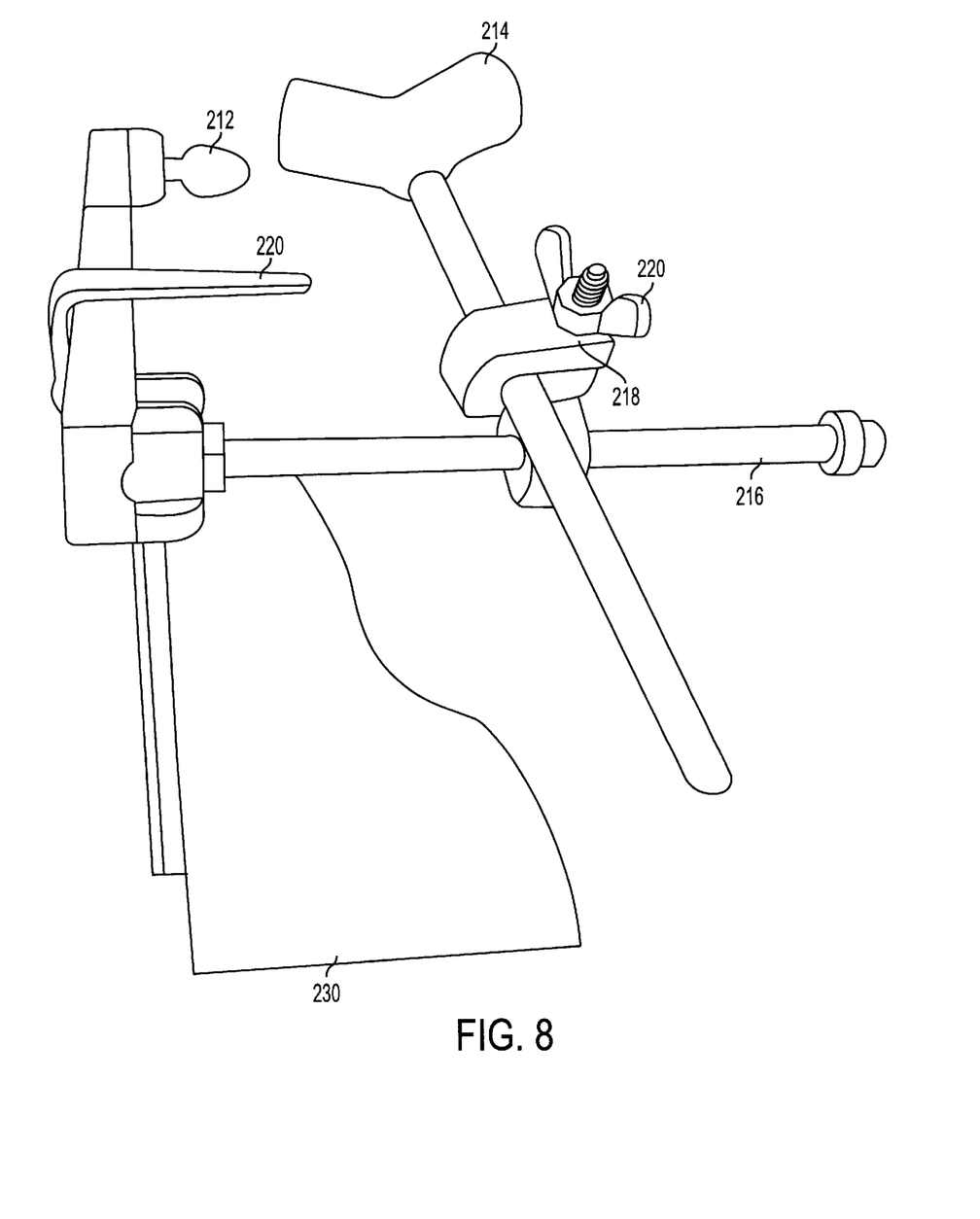
FIG. 8 shows the top bar of the gauge shown in FIG. 7.
Figure 9:
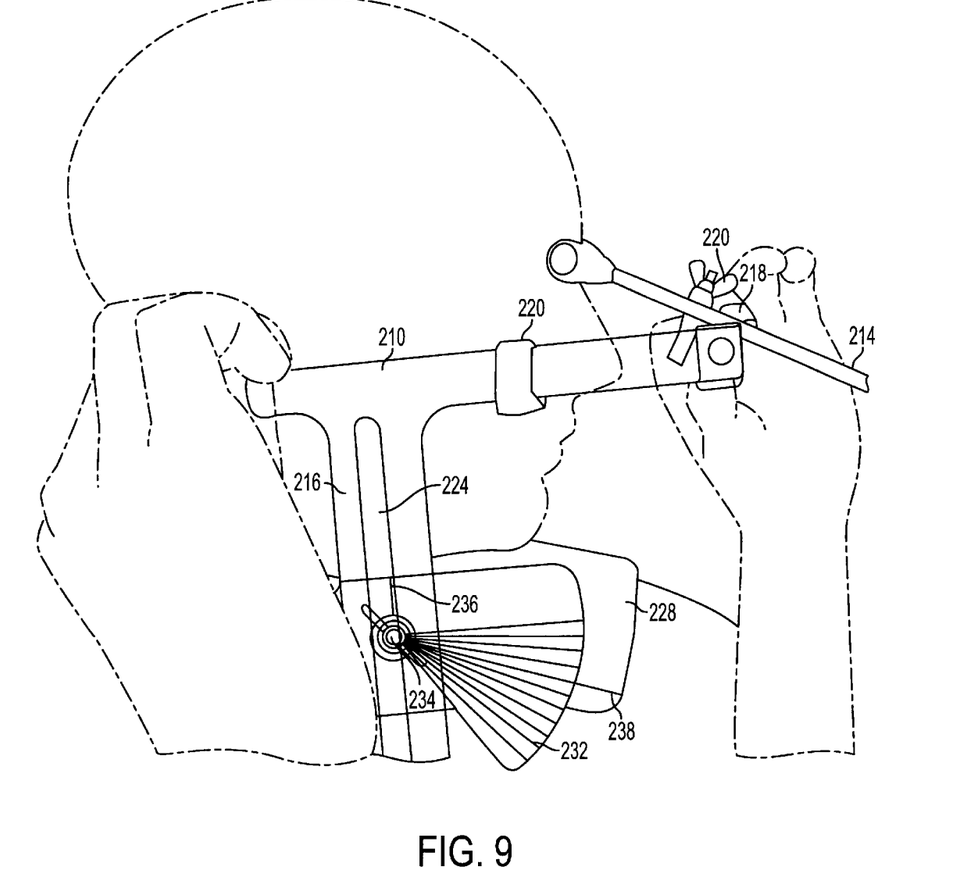
FIG. 9 shows the gauge of FIG. 7 when correctly aligned and adjusted on a patient.
Figure 10:
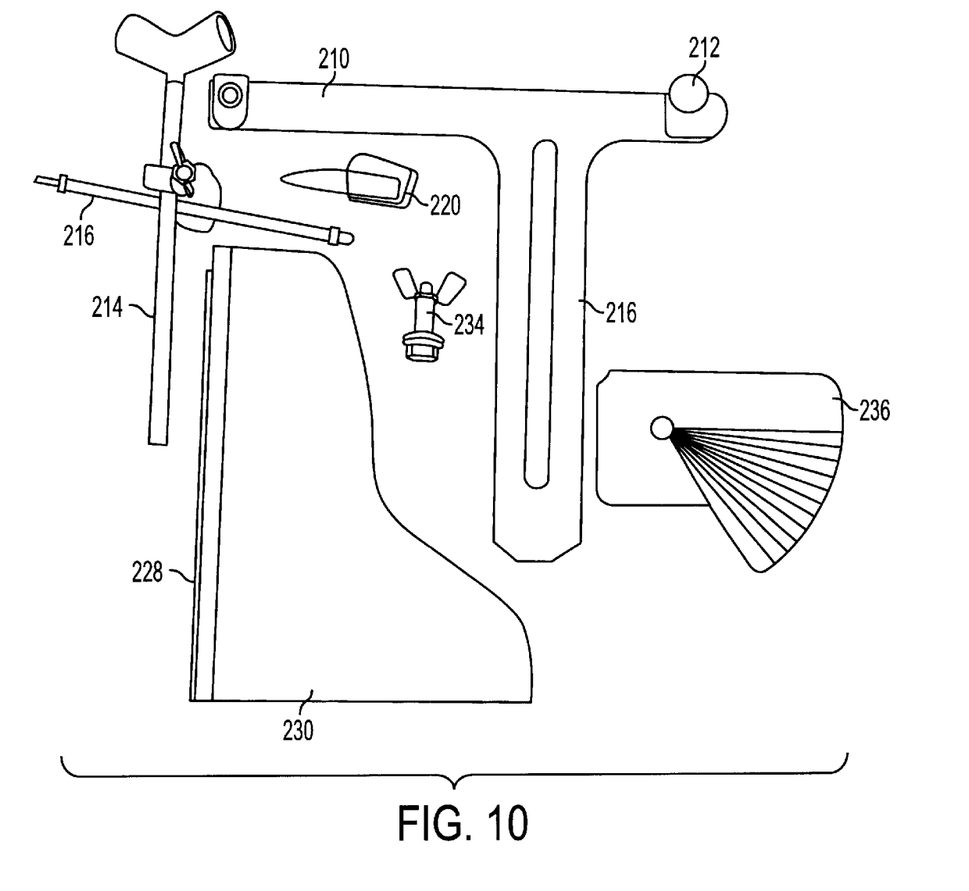
FIG. 10 shows the gauge of FIG. 7 disassembled.

FIG. 7 shows gauge 200 according to the present invention. Gauge 200 measures FMA directly, rather than via rulers and a conversion table. Analogous parts to the FIG. 1 embodiment are similar in form and function. As best shown in FIG. 8, upper bar 210 includes earpiece 212, nosepiece 214, nosepiece bar 216, universal joint 218, and infraorbital indicator 220. When adjusted to the patient, infraorbital indicator 220 is aligned with the patient's orbitale (as shown in FIG. 9) and earpiece 212 fits into the patient's ear, wingnut 222 of universal joint 218 loosened and nosepiece 214 is adjusted so that its dumbbell-shaped end straddles the bridge of the patient's nose (see FIG. 9).

Downward bar depends from upper bar 210, and extends to or below the level of the patient's gonion when gauge 200 is properly aligned with the patient. Slot 224 on downward bar 216, together with longitudinal slot 226 of lower bar 228 allows for vertical and horizontal adjustment of lower bar 228 and attached mandibular plate 230 with respect to downward bar 216. Mandibular plate 230 moves in unison with lower bar 228, and, if desired, lower bar 228 and mandibular plate 230 may be a unitary piece.

Angulation indicator 232 is attached to lower bar 228 and mandibular plate 230 with wingnut 234. Angular indicator 232 includes angular markings thereon. In use, wingnut 234 is loosened and angular indicator is set so that the "0" angle line is parallel to upper bar 210. This alignment can be aided by line 236 which is fully within slot 224 of downward bar 216 when the "0" angle line is parallel to upper bar 210. Gauge 200 is aligned with the patient as described above and mandibular plate 230/lower bar 228 are adjusted so that lower bar 228 parallels the patient's gonion-menton line (see FIG. 9), typically by adjusting the device so that the mandibular plate is against the lower border of the mandible. The wingnut is then tightened. To check for correct adjustment, the patient may be asked whether he or she feels contact with the back and front of the underside of the lower jaw. The top bar is then securely held while the FMA is then read by noting the intersection of a mark (in this case longitudinal indicator line 238 with the angular markings on angulation indicator 232. Repeated adjustments and readings may be taken to insure consistency and accuracy. As shown in FIG. 9, gauge 200 may be easily disassembled for storage and disinfection.

In all embodiments, the frame is typically made of a rigid material, such as a stainless steel or hard plastic, to reduce the possibility of inaccuracy due to flexing. Additionally, if desired, the device may be made of autoclavable material. Gauges made of autoclavable materials (e.g., stainless steel) may be desirable if use of the gauge during surgical procedures is envisioned.

Obviously, many modifications and variations of the present invention are possible in light of the above teachings. It is therefore to be understood that, within the scope of the appended claims, the invention may be practiced otherwise than as specifically described.

What is claimed is:

1. A gauge for measuring the Frankfurt Mandibular Angle of a patient when positioned on along the side of said patient's head, comprising:
    a frame, said frame being defined by:
        an upper bar adapted to extend parallel to and at the same height of a line extending from said patient's orbitale to said patient's porion, said upper bar extending from said porion to at least said orbitale;
        a front bar attached to said upper bar at a fixed location and angle and extending downwardly therefrom to at least a point below said patient's menton, said front bar having a measuring device for indicating distance along the length of said front bar;
        a rear bar attached, rearward of said front bar, to said upper bar at a fixed location and angle and extending downwardly therefrom to at least a point below said patient's gonion, said rear bar having a measuring device for indicating distance along the length of said rear bar;
        a lower bar movably attached to said front and rear bars so that said lower bar may be upwardly or downwardly moved with respect to said front and rear bars and said lower bar may be positioned parallel to and at the same height of a line extending between said patient's menton and said gonion, said lower bar extending at least between said menton and said gonion, said lower bar being lockable along said front and said bars once so positioned, and intersecting said rear bar and said front bar at positions reportable by said respective measuring devices.

2. The gauge of claim 1, further comprising an earpiece fixed to said upper bar and adapted to fit into the ear of said patient that is proximal to said upper bar.

3. The gauge of claim 1, further comprising a plate, adjustably attached to said lower bar so as to firmly contact the mandible of said patient when said lower bar is positioned parallel to and at the same height of a line extending between said patient's menton and said gonion.

4. The gauge of claim 1, wherein said front bar and said rear bar are parallel to each other.

5. The gauge of claim 4, wherein said front bar and rear bar are perpendicular to said upper bar.

6. The gauge of claim 1, further comprising:
    a nosepiece slide attached to said upper bar, said nosepiece slide extending away from said frame toward the side of said patient's head opposite said frame;
    a nosepiece adjustably attached to said nosepiece slide so that said nosepiece fits in the bridge of said patient's nose when said upper bar is positioned parallel to and at the same height of a line extending between said patient's porion and said orbitale.

7. The gauge of claim 6, wherein one end of said nosepiece is dumbbell-shaped.

8. The gauge of claim 1, further comprising a support bar beneath said lower bar, said support bar being fixed to and coplanar with said rear bar and said front bar.

9. The gauge of claim 1, wherein said measuring device on said front bar comprises graduations defining a scale indicating distance along the length of said front bar and said measuring device on said rear bar comprises graduations defining a scale indicating distance along the length of said rear bar.

10. The gauge of claim 9, wherein said lower bar is transparent where said lower bar intersects said rear bar and where said lower bar intersects said front bar, so that said gradations on said front bar and said gradations on said lower bar are visible through said lower bar.

11. The gauge of claim 1, wherein said upper bar, said lower bar, said front bar, and said rear bar, are sterilizable.

12. The gauge of claim 1, wherein said frame is trapezoidal.

13. A gauge for measuring the Frankfurt Mandibular Angle of a patient when positioned on along the side of said patient's head, comprising:
    a trapezoidal frame, said trapezoidal frame being defined by:
        a sterilizable upper bar adapted to extend parallel to and at the same height of a line extending from said patient's orbitale to said patient's porion, said upper bar extending from said porion to at least said orbitale;
        a sterilizable front bar attached to said upper bar at a fixed location and extending perpendicularly therefrom to at least a point below said patient's menton, said front bar having thereon graduations defining a scale indicating distance along the length of said front bar;
        a sterilizable rear bar attached, rearward of said front bar, to said upper bar at a fixed location and extending perpendicularly therefrom to at least a point below said patient's gonion, said front bar having thereon graduations defining a scale indicating distance along the length of said rear bar;
        a sterilizable lower bar movably attached to said front and rear bars so that said lower bar may be upwardly or downwardly moved with respect to said front and rear bars and said lower bar may be positioned parallel to and at the same height of a line extending between said patient's menton and said gonion, said lower bar extending at least between said menton and said gonion, said lower bar being lockable along said front and said bars once so positioned, and intersecting said upper bar and said lower bars at positions having said gradations thereon, said lower bar being transparent where said lower bar intersects said rear bar and where said lower bar intersects said front bar, so that said gradations on said front bar and said gradations on said lower bar are visible through said lower bar;
    an earpiece fixed to said upper bar and adapted to fit into the ear of said patient that is proximal to said upper bar;
    a sterilizable plate, adjustably attached to said lower bar so as to firmly contact the mandible of said patient when said lower bar is positioned parallel to and at the same height of a line extending between said patient's menton and said gonion;
    a nosepiece slide attached to said upper bar, said nosepiece slide extending away from said frame toward the side of said patient's head opposite said frame;
    a nosepiece, said nosepiece having a dumbbell-shaped end and being adjustably attached to said nosepiece slide so that said dumbbell-shaped end of said nosepiece fits in the bridge of said patient's nose when said upper bar is positioned parallel to and at the same height of a line extending between said patient's porion and said orbitale; and
    a sterilizable support bar beneath said lower bar, said support bar being fixed to and coplanar with said rear bar and said front bar.

14. A gauge for measuring the Frankfurt Mandibular Angle of a patient when positioned on along the side of said patient's head, comprising:

a rigid framework, said rigid framework being defined by:
an upper bar adapted to extend parallel to and at the same height of a line extending from said patient's orbitale to said patient's porion, said upper bar extending from said porion to at least said orbitale;
a downward bar attached to said upper bar at a fixed location and angle and extending downwardly therefrom to at least a point below an imaginary line extending from said patient's menton to said patient's gonion;
a lower bar movably attached to said downward bar so that said lower bar may be upwardly or downwardly moved with respect to said upper bar and said lower bar may be positioned parallel to and at the same height of a line extending between said patient's menton and said gonion, said lower bar extending at least between said menton and said gonion, said lower bar being lockable along said downward bar once so positioned; and
a measuring device that measures the angle between said lower bar and said downward bar.

15. The gauge of claim 14, wherein said downward bar is perpendicular to said upper bar.

16. The gauge of claim 14, wherein said measuring device is located on said downward bar.

17. The gauge of claim 14, further comprising an earpiece fixed to said upper bar and adapted to fit into the ear of said patient that is proximal to said upper bar.

18. The gauge of claim 14, further comprising a plate, adjustably attached to said lower bar so as to firmly contact the mandible of said patient when said lower bar is positioned parallel to and at the same height of a line extending between said patient's menton and said gonion.

19. The gauge of claim 14, further comprising:
a nosepiece slide attached to said upper bar, said nosepiece slide extending away from said frame toward the side of said patient's head opposite said frame;
a nosepiece adjustably attached to said nosepiece slide so that said nosepiece fits in the bridge of said patient's nose when said upper bar is positioned parallel to and at the same height of a line extending between said patient's porion and said orbitale.

20. The gauge of claim 14, wherein one end of said nosepiece is dumbbell-shaped.

21. The gauge of claim 14, wherein said upper bar, said lower bar, said front bar, and said rear bar, are sterilizable.

22. The gauge of claim 14, wherein said measuring device includes an angular indicator that moves said upwardly or downward along the downward bar responsive to the corresponding movement of said lower bar and in the same direction as said lower bar.

23. The gauge of claim 14, wherein said measuring device includes an electronic sensor that detects the angular relationship between said downward bar and said lower bar.

24. A gauge for measuring the Frankfurt Mandibular Angle of a patient when positioned on along the side of said patient's head, comprising:
a rigid framework, said rigid framework being defined by:
a sterilizable upper bar adapted to extend parallel to and at the same height of a line extending from said patient's orbitale to said patient's porion, said upper bar extending from said porion to at least said orbitale;
a sterilizable downward bar attached to said upper bar at a fixed location and extending downwardly and perpendicularly therefrom to at least a point below an imaginary line extending from said patient's menton to said patient's gonion;
a sterilizable lower bar movably attached to said downward bar so that said lower bar may be upwardly or downwardly moved with respect to said upper bar and said lower bar may be positioned parallel to and at the same height of a line extending between said patient's menton and said gonion, said lower bar extending at least between said menton and said gonion, said lower bar being lockable along said downward bar once so positioned;
a nosepiece slide attached to said upper bar, said nosepiece slide extending away from said frame toward the side of said patient's head opposite said frame;
a nosepiece, said nosepiece having a dumbbell shaped end and being adjustably attached to said nosepiece slide so that said dumbbell-shaped end of said nosepiece fits in the bridge of said patient's nose when said upper bar is positioned parallel to and at the same height of a line extending between said patient's porion and said orbitale;
an earpiece fixed to said upper bar and adapted to fit into the ear of said patient that is proximal to said upper bar;
a plate, adjustably attached to said lower bar so as to firmly contact the mandible of said patient when said lower bar is positioned parallel to and at the same height of a line extending between said patient's menton and said gonion; and
an angular indicator that measures the angle between said lower bar and said downward bar an angular indicator and that moves said upwardly or downward along the downward bar responsive to the corresponding movement of said lower bar and in the same direction as said lower bar.

25. A method of measuring the Frankfurt Mandibular Angle of a patient, comprising the steps of:
selecting a gauge comprising a frame, said frame including an upper bar, front bar attached at a fixed location and angle and extending downwardly from said upper bar, and a rear bar attached, rearward of said front bar, to said upper bar at a fixed location and angle and extending downwardly therefrom, and a lower bar movably attached to said front bar and said rear, said front bar and said rear bar having measuring devices for indicating distance along the length of said front bar or said rear bar, respectively, said lower bar intersecting said rear bar and said front bar at positions reportable by said respective measuring devices;
positioning said frame along one side of said patient's head so that said upper bar extends parallel to and at the same height of a line extending from said patient's orbitale to said patient's porion with said upper bar extending from said porion to at least said orbitale, said front bar extends to at least a point below said patient's menton, said rear bar extends to at least a point below said patient's gonion;
adjusting said lower bar vertically with respect to said front and rear bars so that said lower bar is parallel to and at the same height of a line extending between said patient's menton and said gonion, said lower bar extending at least between said menton and said gonion;
locking said lower bar along said front bar and said rear bar once so adjusted;
correlating the vertical positions of said adjusted lower bar along said front bar and said rear bar, as reported by said measuring device, with the Frankfort Mandibular Angle of said patient.

26. The method of claim 25, wherein said gauge further comprises an earpiece fixed to said upper bar and further comprising the step of fitting said earpiece into the ear of said patient that is proximal to said upper bar.

27. The method of claim 25, wherein said gauge includes a plate adjustably attached to said lower bar, and further comprising the step firmly contacting said plate with the mandible of said patient when said lower bar is positioned parallel to and at the same height of a line extending between said patient's menton and said gonion.

28. The method of claim 25, wherein said wherein said front bar and said rear bar are parallel to each other.

29. The method of claim 28, wherein front bar and rear bar are perpendicular to said upper bar.

30. The method of claim 25, wherein said gauge further comprises:

a nosepiece slide attached to said upper bar, said nosepiece slide extending away from said frame toward the side of said patient's head opposite said frame;

a nosepiece having a dumbbell-shaped end adjustably attached to said nosepiece slide; and further comprising the step of fitting said dumbell-shaped end of said nosepiece in the bridge of said patient's nose with said upper bar parallel to and at the same height of a line extending between said patient's porion and said orbitale.

31. The method of claim 25, wherein:

said upper and lower bars are sterilizable, said front bar and said rear bar are sterilizable and perpendicular to said upper bar, said measuring device on said front bar comprises graduations defining a scale indicating distance along the length of said front bar, said measuring device on said rear bar comprises graduations defining a scale indicating distance along the length of said rear bar;

said gauge further comprises a support bar beneath said lower bar, said support bar being fixed to and coplanar with said rear bar and said front bar; an earpiece fixed to said upper bar; a plate adjustably attached to said lower bar; a nosepiece slide attached to said upper bar, said nosepiece slide extending away from said frame toward the side of said patient's head opposite said frame; a nosepiece adjustably attached to said nosepiece slide;

and further comprising the steps of:

fitting said earpiece into the ear of said patient that is proximal to said upper bar;

fitting said nosepiece in the bridge of said patient's nose with said upper bar parallel to and at the same height of a line extending between said patient's porion and said orbitale; and firmly contacting said plate with the mandible of said patient when said lower bar is positioned parallel to and at the same height of a line extending between said patient's menton and said gonion.

32. The method of claim 25, wherein said frame is trapezoidal.

33. A method of measuring the Frankfort Mandibular Angle of a patient, comprising the steps of:

selecting a gauge comprising a rigid framework, said rigid framework including:

an upper bar, a downward bar attached to said upper bar at a fixed location and angle and extending downwardly therefrom to at least a point below an imaginary line extending from said patient's menton to said patient's gonion and a lower bar movably attached to said downward bar; and an angular indicator which indicates the angle between said lower bar and said downward bar positioning said framework along one side of said patient's head so that said upper bar extends parallel to and at the same height of a line extending from said patient's orbitale to said patient's porion with said upper bar extending from said porion to at least said orbitale and said downward bar extends to at least a point below said patient's gonion;

adjusting said lower bar vertically with respect to said downward bar so that said lower bar is parallel to and at the same height of a line extending between said patient's menton and said gonion, said lower bar extending at least between said menton and said gonion;

locking said lower bar along said downward bar once so adjusted; and correlating the angle between said adjusted lower bar and said downward bar, as indicated by said measuring device, with the Frankfort Mandibular Angle of said patient.

34. The method of claim 33, wherein said gauge further comprises an earpiece fixed to said upper bar and further comprising the step of fitting said earpiece into the ear of said patient that is proximal to said upper bar.

35. The method of claim 33, wherein said gauge includes a plate adjustably attached to said lower bar, and further comprising the step firmly contacting said plate with the mandible of said patient when said lower bar is positioned parallel to and at the same height of a line extending between said patient's menton and said gonion.

36. The method of claim 33, wherein said downward bar is perpendicular to said upper bar;

said upper and lower bars are sterilizable, said downward bar is sterilizable and perpendicular to said upper bar, said measuring device includes an electronic sensor that detects the angular relationship between said downward bar and said lower bar;

said gauge further comprises a support bar beneath said lower bar, said support bar being fixed to and coplanar with said downward bar; an earpiece fixed to said upper bar; a plate adjustably attached to said lower bar; a nosepiece slide attached to said upper bar, said nosepiece slide extending away from said frame toward the side of said patient's head opposite said frame; a nosepiece adjustably attached to said nosepiece slide;

and further comprising the steps of:

fitting said earpiece into the ear of said patient that is proximal to said upper bar;

fitting said nosepiece in the bridge of said patient's nose with said upper bar parallel to and at the same height of a line extending between said patient's porion and said orbitale; and firmly contacting said plate with the mandible of said patient when said lower bar is positioned parallel to and at the same height of a line extending between said patient's menton and said gonion.

* * * * *